US00PP29931P3

(12) United States Plant Patent
Denardi et al.

(10) Patent No.: US PP29,931 P3
(45) Date of Patent: Dec. 4, 2018

(54) APPLE TREE NAMED 'LUIZA'

(50) Latin Name: *Malus domestica*
Varietal Denomination: Luiza

(71) Applicant: Empresa de Pesquisa Agropecuária e Extensão Rural de Santa Catarina (Epagri), Florianópolis, Santa Catarina (BR)

(72) Inventors: Frederico Denardi, Caçador (BR); Marcus Vinicius Kvitschal, Caçador (BR); Maraisa Crestani Hawerroth, Caçador (BR)

(73) Assignee: Empresa de Pesquisa Agropecuaria e Extensao Rural de Santa Catarina (EPAGRI), Florianopolis, Santa Catarina (BR)

( * ) Notice: Subject to any disclaimer, the term of this patent is extended or adjusted under 35 U.S.C. 154(b) by 0 days.

(21) Appl. No.: 14/999,705

(22) Filed: Jun. 15, 2016

(65) Prior Publication Data
US 2017/0367230 P1 Dec. 21, 2017

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'Luiza' apple tree (*Malus domestica* Borkh) is a new variety selected for its low chilling requirement, resistance to Gala leaf spot disease, high fruit quality, and early fruit maturity.

3 Drawing Sheets

Latin name: *Malus domestica.*
Variety denomination: 'Luiza'.

BACKGROUND OF THE VARIETY

'Luiza' is a new and distinct variety of apple tree (*Malus domestica* Borkh) obtained from a controlled cross of 'Imperatriz' (female parent, not patented) x 'Cripps Pink' (male parent, U.S. Plant Pat. No. 7,880) carried out at Caçador, Santa Catarina, Brazil in 2001. Seeds obtained from the cross were planted at Caçador, and 'Luiza' was selected from the resulting seedlings for propagation and further observation. 'Luiza' was first asexually propagated by grafting in 2004 at Caçador, and has since been observed to remain true to type over successive asexually propagated generations.

BRIEF DESCRIPTION OF THE VARIETY

'Luiza' apple tree is distinguished by its resistance to Gala leaf spot disease (*Colletotrichum* spp.) and its low chilling requirement. Fruit of 'Luiza' is notable for its high quality, having crisp juicy flesh and a high sugar content. Fruit of 'Luiza' ripens earlier than comparable varieties.

'Luiza' is distinguished from female parent 'Imperatriz' by its earlier ripening; more intense skin color; and higher sugar content.

'Luiza' is distinguished from male parent 'Cripps Pink' by its lower chilling requirement; earlier fruit maturity; higher level of juiciness, crispness and sugar; lower acidity; deeper red skin color; and resistance to Gala leaf spot disease.

'Luiza' is distinguished from standard 'Gala', a similar variety, by its lower chilling requirement; resistance to Gala leaf spot disease; less prominent striping and more complete and intense overcolor; and production of fruit predominantly on spur buds, as compared to 'Gala', which produces fruit on both spur buds and terminal buds of long shoots.

BRIEF DESCRIPTION OF THE PHOTOGRAPHS

The accompanying photographs of the 'Luiza' variety were taken from 2013 to 2015 at Caçador, Brazil.

DETAILED BOTANICAL DESCRIPTION OF THE VARIETY

Figure 1:
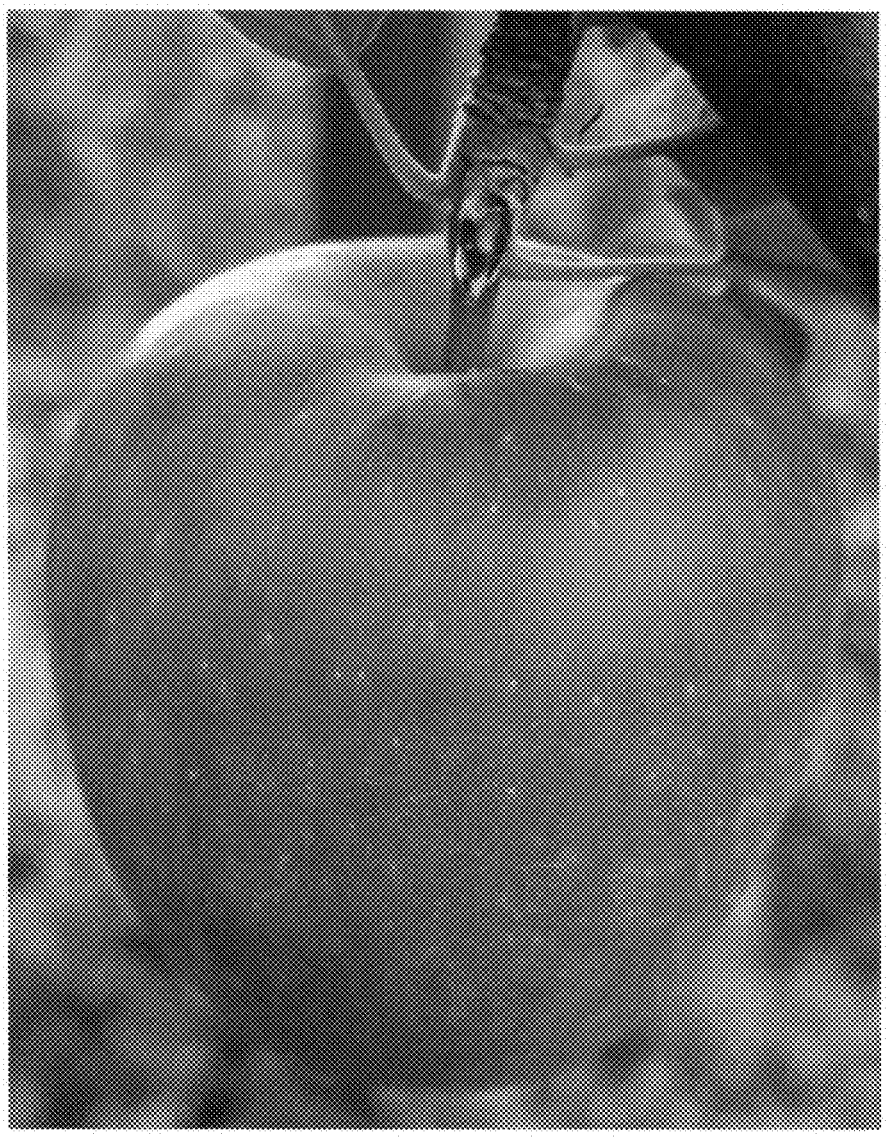
FIG. 1 is a photograph of a 'Luiza' apple.
Figure 2:
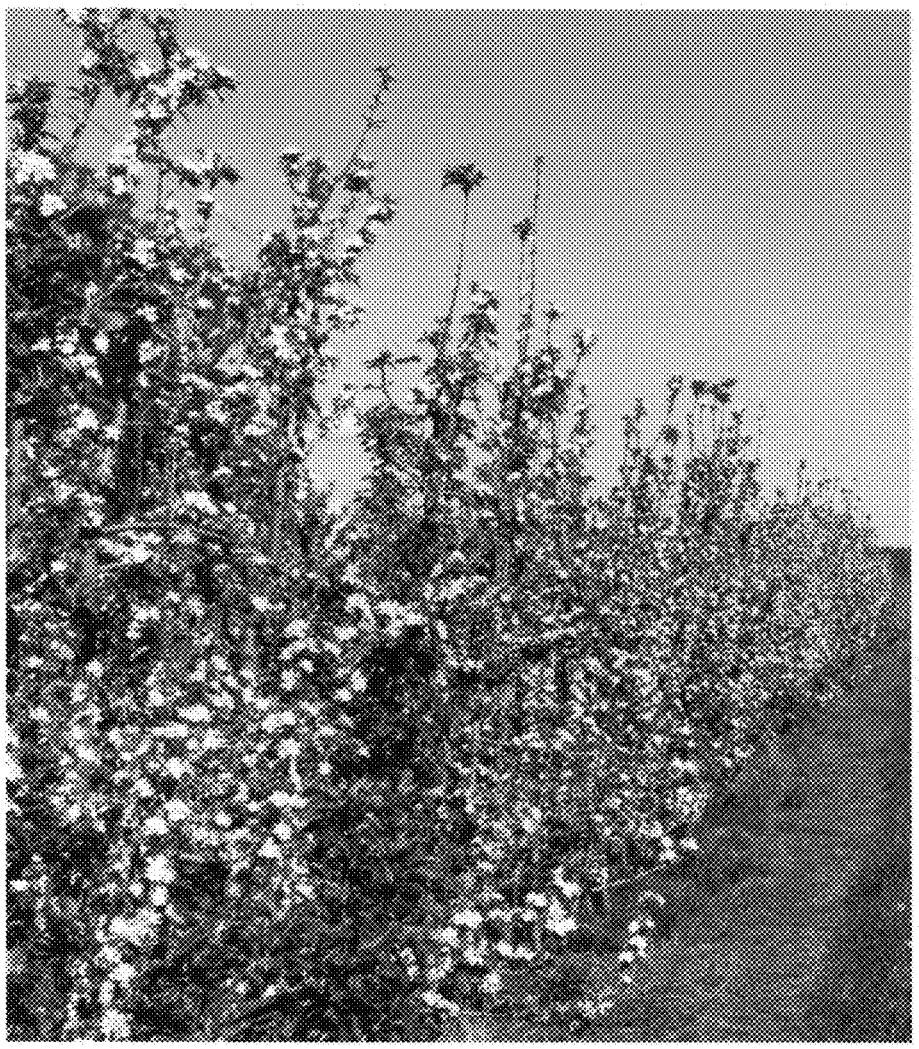
FIG. 2 is a photograph of 'Luiza' apple trees in bloom.
Figure 3:
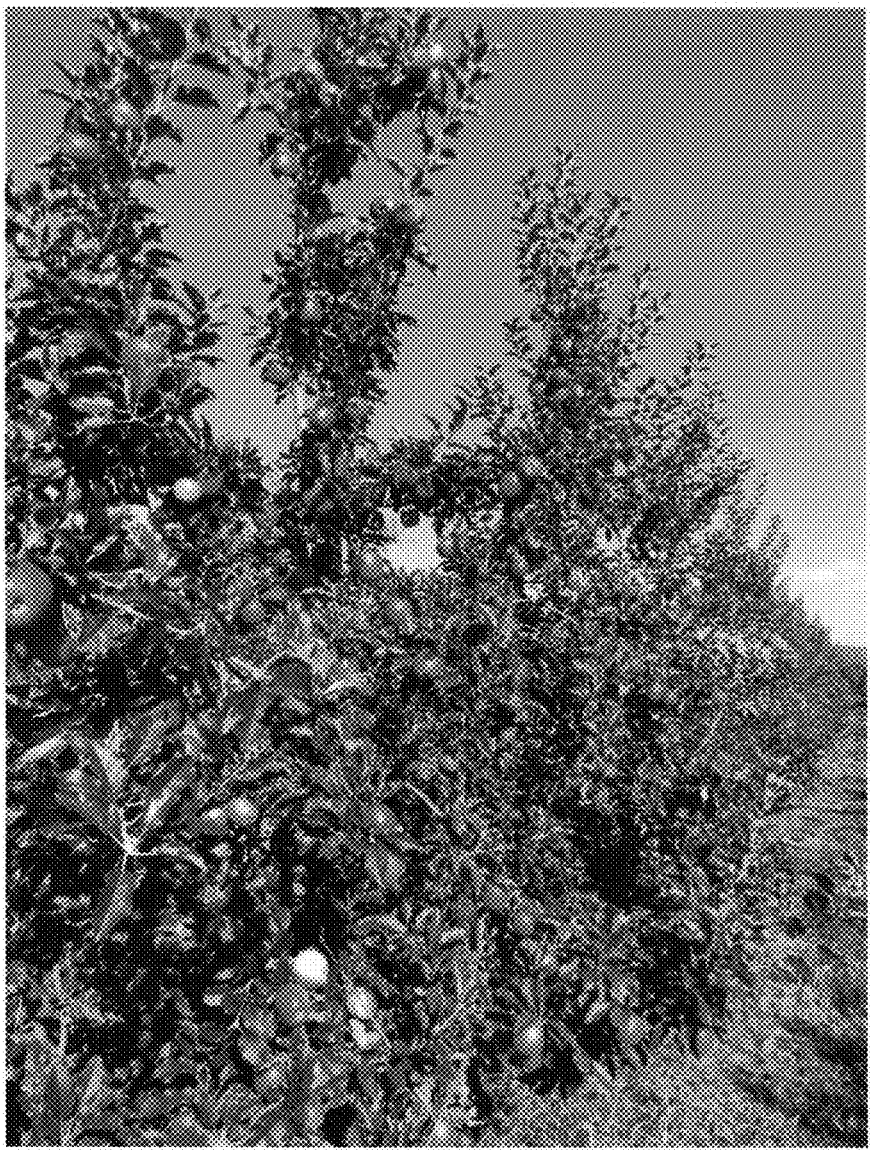
FIG. 3 is a photograph of 'Luiza' apple trees and fruit.

The following-detailed botanical description is based on observations made at Caçador, Brazil from 2013 to 2015, of trees planted in 2011, grown on 'Marubakaido' rootstock (not patented) with 'M-9' interstock (not patented). All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Medium.
*Type*.—Ramified.
*Habit*.—Spreading.
*Height*.—3.8 m.
*Trunk diameter* (*at* 30 *cm above the graft*).—8.8 cm.
*Bark texture*.—Smooth.
*Bark color*.—Yellow green 152B.
*Trunk lenticel length*.—3.0 mm.
*Trunk lenticel height*.—1.1 mm.
*Trunk lenticel shape*.—Elliptical.
*Trunk lenticel color*.—Yellow white 158A.
*Trunk lenticel density*.—5.9 lenticels/$cm^2$.

Branch (fruiting branches located at around 1 m above the graft union):
*Length*.—1.3 m.
*Diameter*.—2.5 cm.
*Crotch angle*.—70° to 80°.
*Bark color*.—Greyed-green 198A.
*Lenticel diameter*.—1.0 mm.
*Lenticel shape*.—Round.
*Lenticel color*.—Greyed-yellow 162A.
*Number of lenticels per* $cm^2$.—5.4.

One year old shoot:
*Length*.—0.8 m.
*Color*.—Greyed-brown 199B.
*Pubescence*.—Weak.
*Thickness*.—6.7 mm.
*Internode length*.—2.4 cm.
*Number of lenticels per* $cm^2$.—2.7.

Flower buds:
*Quantity per spur*.—1.6.
*Shape*.—Spiky.
*Length*.—8.8 mm.
*Diameter*.—4.5 mm.
*Color*.—Greyed-orange 166A.
*Date of first bloom*.—September 10 to 18.
*Date of full bloom*.—September 25 to October 3.
*Pollination requirement*.—Yes.

Flowers:
*Diameter of fully open flower*.—37.2 mm.
*Relative position of petal margin*.—Intermediate.
*Number per cluster*.—About 5.
*Flower height*.—17.6 mm.
*Flower fragrance*.—Low.

Petals:
*Number per flower*.—5.
*Shape*.—Wide-elliptic.
*Length*.—18.7 mm.
*Width*.—14.7 mm.
*Apex shape*.—Rounded.
*Base shape*.—Rounded.
*Margin*.—Smooth.
*Color of upper surface*.—White NN155D, with spots of Red-purple 70C.
*Color of lower surface*.—White NN155D, with spots of Red-purple 68A.

Pistils:
*Length*.—3.8 mm.
*Quantity*.—5.
*Color*.—Green-white 157B.

Stigma:
*Length*.—0.6 mm.
*Color*.—Yellow-green N144D.

Style:
*Length*.—3.8 mm.
*Color*.—Yellow-green N144D.

Ovary:
*Size*.—3.64 mm wide×4.23 mm long.
*Color*.—Greyed-green 193A.

Anthers:
*Quantity*.—14.7 anthers per flower.
*Anther length*.—2.1 mm.
*Anther width*.—1.4 mm.
*Anther color*.—Yellow 8B.
*Presence of pollen*.—Yes.
*Pollen quantity*.—Abundant.
*Color of pollen*.—Yellow 8B.

Pedicel:
*Length*.—16.9 mm.
*Diameter*.—2.7 mm.
*Color*.—Yellow-green 144B.

Sepals:
*Quantity*.—5 per flower.
*Sepal color*.—Upper surface — Green 143D.
*Sepal color*.—Lower surface — Yellow-green 145A.
*Sepal shape*.—Acuminate.
*Sepal width*.—5.3 mm.
*Sepal length*.—10.7 mm.
*Sepal apex shape*.—Pointed.
*Sepal margin*.—Smooth and pubescent.

Leaves:
*Shape*.—Ovate.
*Length*.—10.3 cm.
*Width*.—5.4 cm.
*Length/width ratio*.—1.9.
*Leaf texture*.—Upper surface — Smooth.
*Leaf texture*.—Lower surface — Velvety.
*Leaf venation pattern*.—Cross-venulate.
*Leaf vein color*.—Upper surface — Yellow-green 145B.
*Leaf vein color*.—Lower surface — Yellow-green 145C.
*Blade margin*.—Serrate.
*Apex shape*.—Acute.
*Base shape*.—Rounded.
*Color of upper surface*.—Green N137A.
*Color of lower surface*.—Yellow-green 147C.
*Attitude in relation to shoot*.—Upward.

Petiole:
*Length*.—27 mm.
*Diameter*.—2 mm.
*Color*.—Yellow-green 146C.

Fruit:
*Quantity per cluster*.—3 to 5.
*Diameter*.—69 mm.
*Height*.—69 mm.
*Weight*.—170 g.
*Ratio of height to width*.—1.
*General shape in profile*.—Conical.
*Position of maximum diameter*.—On the third near to the stalk cavity.
*Ribbing*.—Medium.
*Crowning at calyx end*.—Medium.
*Diameter of eye*.—6 mm.
*Length of sepal*.—7 mm.
*Bloom of skin*.—Absent to weak.
*Greasiness of skin*.—Absent to weak.
*Background color of skin*.—Yellow 4A.

*Over color of skin.*—Red 46A.
*Amount of over color.*—70% to 80%.
*Intensity of over color.*—Medium.
*Pattern of over color.*—Solid flush with strongly defined stripes.
*Amount of russet around stalk cavity.*—Very small.
*Amount of russet on cheeks.*—Absent.
*Area of russet around eye basin.*—Absent.
*Length of stalk.*—20 mm.
*Thickness of stalk.*—6 mm.
*Stalk color.*—Yellow-green 152C.
*Depth of stalk cavity.*—11 mm.
*Width of stalk cavity.*—19 mm.
*Depth of eye basin.*—10 mm.
*Width of eye basin.*—26 mm.
*Fruit locule quantity.*—5.
*Fruit locule length.*—24.2 mm.
*Fruit locule width.*—4.4 mm.
*Firmness of flesh.*—17 to 18 pounds.
*Flesh texture.*—Fine.
*Aroma.*—Medium.
*Juiciness.*—Very juicy.
*Brix.*—13.0 to 13.5° Brix.
*Flesh color.*—Yellow 11C.

Seeds:
*Quantity per fruit.*—8.
*Seed length.*—14.6 mm.
*Seed width.*—4.2 mm.
*Shape.*—Ovate.
*Color.*—Brown 200B.

Harvest:
*Harvest date* (*actual and relative*).—Early (beginning of February, in Brazil).
*Number of picks.*—Two.
*Amount of fruit produced per tree per harvest.*—18 to 20 Kg per plant.

Disease resistance/susceptibility: Susceptible to apple scab (*Venturia inaequalis*); Resistant to Gala leaf spot (*Colletotrichum* spp.); Tolerant to powdery mildew (*Podosphaera leucotricha*).

Winter hardiness: Hardy in region tested (USDA hardiness zone 11b); Low chilling requirement suitable for climate in region tested.

Market use: Fresh.

We claim:

1. A new and distinct apple tree as described and illustrated herein.

* * * * *